United States Patent [19]
Bourgeois

[11] Patent Number: 6,115,635
[45] Date of Patent: *Sep. 5, 2000

[54] METHOD AND APPARATUS FOR ELECTRICAL STIMULATION OF THE GASTROINTESTINAL TRACT

[75] Inventor: Ivan Bourgeois, Verviers, Belgium

[73] Assignee: Medtronic, Inc., Minneapolis, Minn.

[ * ] Notice: This patent is subject to a terminal disclaimer.

[21] Appl. No.: 09/282,184

[22] Filed: Mar. 31, 1999

Related U.S. Application Data

[62] Division of application No. 08/990,965, Dec. 15, 1997, abandoned.

[51] Int. Cl.$^7$ ............................................... A61N 1/36
[52] U.S. Cl. ................................................. 607/40
[58] Field of Search ....................................... 607/40

[56] References Cited

U.S. PATENT DOCUMENTS

| | | |
|---|---|---|
| 4,981,470 | 1/1991 | Bombeck, IV . |
| 5,188,104 | 2/1993 | Wernicke et al. . |
| 5,292,344 | 3/1994 | Douglas . |
| 5,836,994 | 11/1998 | Bourgeois ............................... 607/40 |
| 5,861,014 | 1/1999 | Familoni .................................. 607/40 |

FOREIGN PATENT DOCUMENTS

| | | |
|---|---|---|
| 2 237 630 | 7/1973 | France . |
| 2 453 630 | 4/1979 | France . |
| 0571 938A2 | 5/1993 | Germany . |
| 1651918A1 | of 0000 | U.S.S.R. . |
| WO 94/27672 | 5/1994 | WIPO . |

OTHER PUBLICATIONS

Ergebnisse der Inneren Medizin und Kinderheilkunde—16:198 (1961) (cover page).

Electric Stimulation of the Gastrointestinal Tract—GP Apr. 1994.

Gastrointestinal Pacing—A New Concept in the Treatment of Ileus—Biomedical Sciences Instrumentation vol. 1. 1963 (A.M. Bilgutay, R. Wingrove, W.O. Griffen, R.C. Bonnabeau and C.W. Lillehei).

Gastro–intestinal Pacing: Will It Work?—American Journal of Surgery, Feb. 1966 (J. Sonneland).

Evaluation of the Intrinsic Innervation of the Internal Anal Sphincter using Electrical Stimulation—Gut, 1989, 30, 935–938 (M.A. Kamm, J.E. Lennard–Jones, and R.J. Nicholls).

(List continued on next page.)

*Primary Examiner*—William E. Kamm
*Attorney, Agent, or Firm*—Thomas F. Woods; Michael J. Jaro; Harold Patton

[57] ABSTRACT

A method and apparatus for providing electrical stimulation of the gastrointestinal tract. The apparatus features an implantable pulse generator which may be coupled to the gastric system through one or more medical electrical leads. In the preferred embodiment the leads couple to the circular layer of the stomach. The pulse generator preferably features sensors for sensing gastric electrical activity, and in particular, whether peristaltic contractions as occurring. One embodiment particularly solves the problem of accurately detecting gastric arrhythmias by periodically reverting into a sensed intrinsic gastric rhythm mode. In this mode the output of electrical stimulation is adjusted to only occur at an exceedingly slow rate. This slow rate of stimulation thus permits the gastro-intestinal tissues to undergo an intrinsic depolarization so that the underlying intrinsic slow wave rate may be detected.

14 Claims, 9 Drawing Sheets

OTHER PUBLICATIONS

Enhancing Absorption in the Canine Short Bowel Syndrome by Instestinal Pacing—Surgery, Aug. 1980 (H.E. Gladen and K.A. Kelly).

Pacing the Human Stomach—Surgery, Feb. 1992 (B.W. Miedema, M.G. Sarr and K.A. Kelly).

Ectopic Jejunal Pacemakers and Gastric Emptying after Roux Gastrectomy: Effect of Intestinal Pacing—Surgery, Nov. 1989 (L.Karlstrom and K.A. Kelly).

A New Treatment for Rectal Prolapse (Abridged)—Proceedings of the Royal Society of Medicine (K.P.S. Caldwell).

Prognosis of Patients with an Ileostomy—Section of Proctology (A.G. Parks).

Differential Responses of the Canine Gastric Corpus and Antrum to Electric Stimulation—American Journal of Physiology, Jan. 1974 (K.A. Kelly).

The Electrical Control of Sphincter Incompetence—The Lancet, Jul. 23, 1963 (K.P.S. Caldwell).

Gastric Motor Physiology and Pathophysiology—Surgical Clinics of North America, vol. 73, Dec. 1993 (J.J. Cullen and K.A. Kelly).

The Role of the Extrinsic Antral Nerves in the Regulation of Gastric Empyting—Surgery, Gynecology & Obstetrics, Sep. 1977, vol. 145 (C.T. Mroz and K.A. Kelly).

A New Treatment for Rectal Prolapse—Geriatrics, Jan. 1968 (K.P.S. Caldwell).

Incontinence—Transactions of The Medical Society of London, Ordinary Meeting, Apr., 1973 (K.P.S. Caldwell).

The Treatment of Incontinence—Hospital Management (K.P.S. Caldwell).

Control of Gastro–intestinal Motility with Electrical Pacing—Jap. J. Smooth Muscle Res. 21: Suppl., 125, 1985 (H.M. Richter, III, S. Bjorck and K.A. Kelly).

Effect of Electrical Stimulation on Gastric Electrical Activity, Motility and Emptying—Neurogastroenterology and Motility 1995 (J.C. Eagon and K.A. Kelly).

Independence of Canine Gastric and Duodenal Pacesetter Potentials Shown by Electric Pacing—May Clin. Proc, Jan. 1977, vol. 52 (H.E. Gladen and K.A. Kelly).

Duodenal–Gastric Refulx and Slowed Gastric Emptying by Electrical Pacing of the Canine Duodenal Pacesetter Potential—Gastroenterology 72:429–433, Mar. 1977 (K.A. Kelly and C.F. Code).

Pacing the Human Gut—The American Journal of Gastroenterology, vol. 89, No. 3, 1994 (D.A. Johnson and E.L. Cattau).

Pacing the Gut—Gastroenterology, Dec. 1992 (K.A. Kelly).

Human Gastric Myoelectric Activity and Gastric Emptying Following Gastric Surgery and With Pacing—1992 Gastroenterological (M.P. Hocking, S.B. Vogel and C.A. Sninsky).

Pacing the Canine Stomach with Electric Stimulation—American Journal of Physiology, Mar. 1972 (K.A. Kelly and R.C. La Force).

Gastric Emptying of Liquids and Solids: Roles of Proximal and Distal Stomach—Editorial Review, The American Physiological Society 1980 (K.A. Kelly).

Electric Pacing of Intact and Transected Canine Small Intestine and its Computer Model—American Journal of Physiology, vol. 229, Nov. 1975 (O.E. Akwari, K.A. Kelly, J.H. Steinbach and C.F. Code).

Electrical Treatment of Anal Incontinence—The Lancet, Feb. 5, 1966 (B.R. Hopkinson, R. Lightwood).

Electrophysiology of Human Colon Motility in Health and Disease—Clinics in Gastroenterology, vol. 15, No. 4, Oct. 1986 (J.D. Huizinga).

Cerebral Evoked Potentials After Rectal Stimulation—Electroencephalography and Clinical Neurophysiology, 80 (1991) 490–495 (V. Loening–Baucke, N.W. Read and T. Yamada).

Measurement of Gastric and Small Bowel Electrical Activity at Laparoscopy—Journal of Laparoendoscopic Surgery, vol.4, No. 5, 1994 (B.O. Familoni, T.L. Abell and G. Voeller).

Electrical Stimulation of the Bowel—Arch Surg. vol. 91, Sep. 1965 (J.M. Moran and D.C. Nabseth).

Electrical Pacing for Short Bowel Syndrome—Surgery, Gynecology & Obstetrics—Nov. 1981, vol. 153 (H.E. Gladen and K.A. Kelly).

The Treatment of Incontinence by Electronic Implants—Annals of The Royal College of Surgeons of England, Dec. 1967 (K.P.S. Caldwell).

The Future of Intestinal Pacing—Gastroenterology Clinics of North America, vol. 23, No. 2, Jun. 1994 (J.J. Cullen and K.A. Kelly).

Control of Muscle Tone in the Human Colon—Gut, 1992, 33, 541–546 (C.J. Steadman, S.F. Phillips, M. Camilleri, N.J. Talley, A. Haddad, R. Hanson).

Enhancing the Anti–Dumping Effect of Roux Gastrojejunostomy with Intestinal Pacing—Ann. Surgery, Oct. 1983, vol. 198 (B. Cranley, K.A. Kelly, V.L.W. Go, L.A. McNichols).

The Roux Operation for Postgastrectomy Syndromes—The American Journal of Surgery, vol. 161, Feb. 1991 (B.W. Miedema, K.A. Kelly).

Effect of Duodenal Cooling on Small Intestinal Pacing—Mayo Clin. Proc. Aug. 1982, vol. 57 (K.R. Berg, H.E. Gladen, K.A. Kelly).

Achieving Enteric Continence: Principles and Applications—Mayo Clin Proc. Jul. 1986, vol. 61 (J.H. Pemberton, K.A. Kelly).

Electrical Stimulation of the Human Stomach—Digestive Diseases and Sciences, vol. 30, No. 8, Aug. 1985 (W.E. Waterfall, D. Miller, D.N. Ghista).

Gastric Electrical Stimulation as a Possible New Therapy for Patients with Severe Gastric Stasis—Gastroenterology, vol. 100, No. 5, Part 2 (T.L. Courtney, B.D. Schirmer, B.E. Ballahsene, O.L. Updike and R.W. McCallum).

Temporary and Permanent Electrical Stimulation of the Human Stomach Using High Frequency Pacing—Motility and Nerve–Gut Interactions, Apr. 1993 (B.O. Familoni, T.L. Abell, G. Voeller, A. Salem, O. Gaber, D. Nemoto).

Long–Term Electrical Stimulation of the Human Stomach—Gastroenterology, vol.106, No. 4, Part 2 (B.O. Familoni, T.L. Abell, G. Voeller, A. Salem, O. Gaber, D. Nemoto).

A Model of Gastric Electrical Activity in Health and Disease—IEEE Transactions on Biomedical Engineering, vol. 42, No. 7, Jul. 1995 (B.O. Familoni, T.L. Abell, K.L. Bowes).

Use of Spectral Analysis in the Detection of Frequency Differences in the Electrogastrograms of Normal and Diabetic Subjects—IEEE Transactions on Biomedical Engineering, vol. 35, No. 11, Nov. 1988 (C.J. Pfister, J.W. Hamilton, N. Nagel, P. Bass, J.G. Webster and W.J. Tompkins).

Gastric Motility after Gastric Operations—Surgery Annual 1974 (K.A. Kelly).

Electrical Stimulation of Gastric Electrical Control Activity—American Journal of Physiology, vol. 225, No. 1, Jul. 1973 (S.K. Sarna and E.E. Daniel).

Electrical Pacing of the Roux Limb Resolves Delayed Gastric Emptying—Journal of Surgical Research 42, 635–641 (1987) (A. Sawchuk, D. Canal, J.L. Grosfeld, <. Slaughter, G. Gardner, T. O'Connor and D. Behrman).

Gastrointestinal Pacing—Staff Report Meeting—University of Minnesota Medical Bulletin 1965 (A.M. Bilgutay, R. Wingrove, W.O. Griffen, A. Nakib, R.C. Bonnabeau, C.W. Lillehei).

Acceleration of Gastric Emptying with Electrical Stimulation in a Canine Model of Gastroparesis—1992 the American Physiology Society (B–E Bellahsène, C.D. Lind, B.S. Schirmer, O.L. Updike and R.W. McCallum).

A Trial of a Gastro–intestinal Pacemaker—Journal of the Irish Medical Association Jan. 1966 (P.N. Fitzpatrick, and A.W. Chen).

Behavioral and Gastrointestinal Changes (Motility and Blood Flow) Induced by Electrical Stimulation of the Lateral Hypothalamus in Cats—Abstr. XI Scand. Physiol. Congr. Copenmhagen 1963, Suppl. No. 213 (F. Björn and E.H. Rubinstein).

Gastrointestinal Pacemaker—The Lancet, Dec. 7, 1963 (J.M. Sanchez).

Gastrointestinal Pacing—Modern Medicine, Mar. 15, 1965 (A.M. Bilgutay, R. Wingrove, W.O. Griffen, A. Nakib, R.C. Bonnabeau and C. W. Lillehei).

Response to Gastrointestinal Pacing: Antral, Duodenal and Jejunal Motility in Control and Postoperative Patients—Annals of Surgery, Jul. 1966 (T. Berger, J. Kewenter, N.G. Kock).

Evaluation of a Portable Gastric Stimulator—IEEE/9th Annual Conference of the Engineering in Medicine and Biology Society, 1987 (B–E. Bellahsene, R.W. McCallum, O.T. Updike).

Role of Gastric Pacesetter Potential Defined by Electrical Pacing—Canadian Journal of Physiology and Pharmacology, vol. 50, Oct. 1972 (K.A. Kelly and R.C. La Force).

The Endomotorsonde—A New Device for Studying the Gastrointestinal Tract—The American Journal of Medical Electronics, Jul.–Sep. 1964 (J.P.M. D'Haens).

Electronic Pacemakers of the Heart, Gastrointestinal Tract, Phrenic Nerve, Bladder and Carotoid Sinus: Current Status—Surgery, Aug. 1966, vol. 60, No. 2 (C.E. Anagnostopoulos, W.W.L. Glenn).

Control of Postoperative Adynamic Bowel in Dogs by Electric Stimulation—vol. IX Trans. Amer. Soc. Artif. Int. Organs, 1963 (D. R. de Villiers, I. Saltiel, A. Nonoyama and A. Kantrowitz).

Reverse Electrical Pacing Improves Intestinal Absorption and Transit Time—Surgery, vol. 100, No.2, Aug. 1986 (A. Sawchuk, W. Nogami, S. Goto, J. Yount, J.A. Grosfeld, J. Lohmuller, M.D. Grosfeld and J.L. Grosfeld).

External Stimulation of Gastric Antrum and Gastric Secretion—The American Journal of Gastroenterology, vol. 52, No. 6, Dec. 1969 (P. Lott, T. Geisel, N.C. Jefferson and H. Necheles).

Electrical Activity of the Gastric Antrum in Normal Human Subjects—The American Journal of Digestive Diseases, vol. 16, No. 7, Jul. 1971 (H. Monges and J. Salducci).

Gastric Pacemakers—Gastroenterology, vol. 70, No. 2, Feb. 1976 (S.K. Sarna, K.L. Bowes and E.E. Daniel).

Apparatus for Electrical Stimulation of Weakened Peristaltic Activity of the Stomach (Experimental Investigation)—Biomedical Eng. Mar.–Apr. 1973 (M.A. Sobakin and V.A. Shepelev).

Clinical Evaluation of the Gastrointestinal Pacer—Surgery, Gynecology & Obstetrics, Jan. 1965 (D.C. Quast, A.C. Beall and M.E. DeBakey).

Electrostimulation of the Small and the Large Bowel in Dogs—Biomedical Sciences Instrumentation, May, 1969 (G. Járos and C.R. Jansen).

Clinical Experience in Control of Postoperative Adynamic Ileus by Electric Stimulation—Surgical Forum, Vo.. 14, 1963 (D.R. de Villiers, I. Saltiel, A. Nonoyama and A. Kantrowitz).

Electric Treatment of Intestinal Obstruction and Postoperative Paralysis of the Bowel—Journ. A.M.A., Apr. 1, 1911 (W.H. Dieffenbach).

Studies in Electrical Stimulation of the Adynamic Bowel—The American Journal of Gastroenterology, vol. 44, 1965 (A. Kantrowitz).

Electrical Activity of the Gastrointestinal Tract as an Indication of Mechanical Activity—American Journal of Digestive Diseases, vol. 8, 1963 (E.E. Daniel and K.M. Chapman).

Relative Electrical Impedance as Index of Intestinal Viability—Archives of Surgery, vol. 89, Jul. 1964 (L.C. Carey, K. Kayser, E. H. Ellison and D. Lepley).

Controlled Radiological Evaluation of an Intestinal Pacemaker (Peristart)—Scand. J. Gastroent., 1966, vol. 1 (P. Bach–Nielsen, H. Baden and A.M. Christensen).

An Improved Method for Recording and Analyzing the Electrical Activity of the Human Stomach—IEEE Transactions on Biomedical Engineering, vol. 32, No. 11, Nov. 1985 (B.E. Bellahsene, J.W. Hamilton, J.G. Webster, P. Bass and M. Reichelderfer).

Study of Transcutaneous and Intraluminal Measurement of Gastric Electrical Activity in Humans—Medical & Biological Engineering & Computing, Jul. 1987 (B.O. Familoni, Y.J. Kingma and K.L. Bowes).

Human Gastric Myoelectric Activity and Gastric Emptying Following Gastric Surgery and With Pacing—Gastroenterology, 1992, vol. 103, No. 6 (M.P. Hocking, S.B. Vogel and C.A. Sninsky).

Programmer Medtronic 7432 and Memory Mod 7455—Clinical Plan Gastroparesis, Mar. 2, 1994.

Electrical Pacing of the Stomach in Dogs—IEEE, Sep. 1992 (B.O. Familoni, T.L. Abell).

Gastroparesis and the Current Use of Prokinetic Drugs—The Gastroenterologist, vol. 1 No. 2, Jun. 1993 (B.J. Kendall and R.W. McCallum).

Physiology of the Colon and Rectum—The American Journal of Surgery, vol. 117, Jun. 1969 (R.D. Williams and J.W. Dickey).

Effects of Gastric Pacing on Canine Gastric Motility and Emptying—American Journal of Physiology, vol. 265, No. 4, Oct. 1993 (J.C. Eagon and K.A. Kelly).

Manometric Evaluation of Children with Chronic Constipation Using a Suction Stimulating Electrode—Eur. J. Pediatr. Surg. 2 (1992)287–290 (M. Kubota, A. Nagasaki and K. Sumitomo).

"High Prevalence of Gastric Electrical Dysrhythmias InDiabetic Gastroparesis"—T.L. Abell et al. (Gastroenterology, 1985; 88:1299).

"Development of a Canine Model for Gastric Pacing"—B.Johnson et al. (Gastroenterology, vol. 98, No. 5, Part 2).

"Postoperative Gastroparesis and Tachygastria—Response to Electric Stimulation and Erythromycin"—M.P. Hocking (Surgery, vol. 114, No.3, Sep. 1993, pp. 538–542).

"Electrogastrographic Study of Gastric Myoelectrical Activity in Patients with Unexplained Nausea and Vomiting"—H. Geldof et al. (Gut, 1986, vol. 27, pp. 799–808).

"Efficacy of Electrical Stimulation at Frequencies Higher than Basal Rate in Canine Stomach"—B. Familoni et al. (Digestive Diseases and Sciences, vol. 42, No. 5, May 1997, pp. 892–897).

"Analysis of Gastric Emptying Data"—J.D. Elashoff et al. (Gastroenterolgy 1982:83; pp. 1306–1312).

"Gastric Myoelectric Activity in Patients with Chronic Idiopathic Gastroparesis"—M. Bortolotti et al. (Gastrointestinal Motility, vol. 2, No. 2, Jun. 1990, pp. 104–108).

GastricElectromechanical and Neurohormonal Function in Anorexia Nervosa: T.L. Abell et al. (Gastroenterology, Nov. 1987:93: pp. 958–965).

Electrogastrography—Current Assessment and Future Perspectives—T.L. Abell et al. (Digestive Diseases and Sciences, vol. 33, No. 8, Aug. 1988, pp. 982–992).

Electrogastrographic Study of Patients with Unexplained Nausea, Bloating and Vomiting—C.H. You et al. (Gastroenterology, vol. 79, No. 2, Aug. 1980, pp. 311 314).

"Motility of the Stomach and Gastroduodenal Junction"—K.A. Kelly (Physiology of the Gastrointestinal Tract, 1981, pp. 393–410).

"Gastric Dysrhythmias and Nausea of Pregnancy"—K.L. Koch et al. (Digestive Diseases and Science, vol. 35, No. 8, Aug. 1990, pp. 961–968).

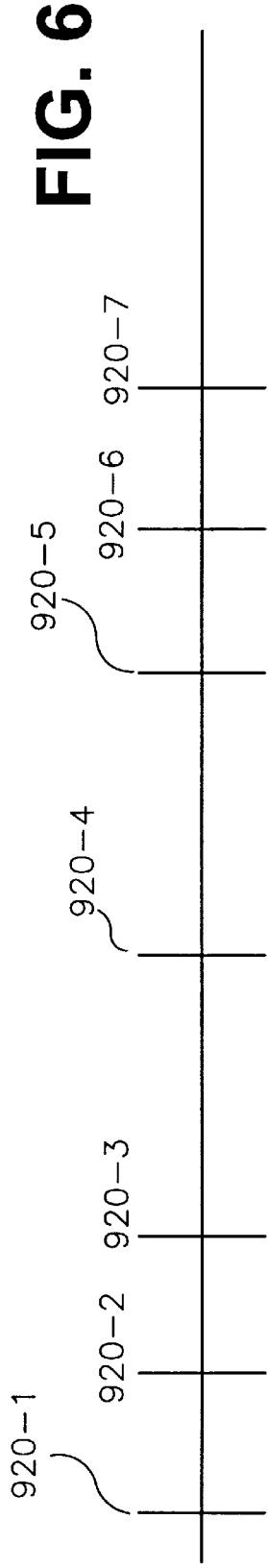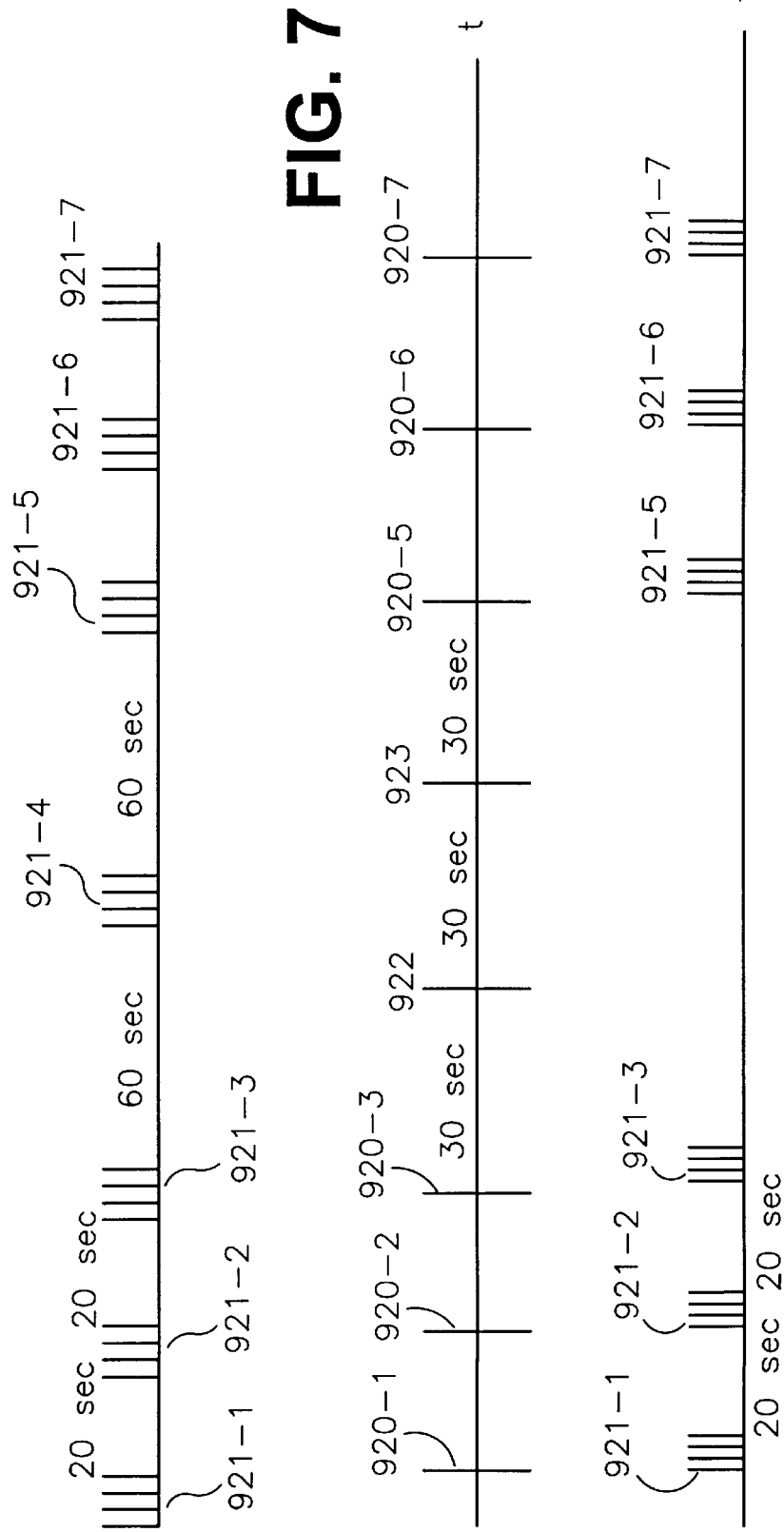

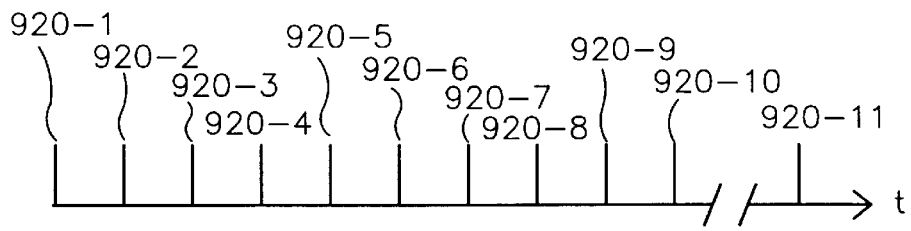
FIG. 8
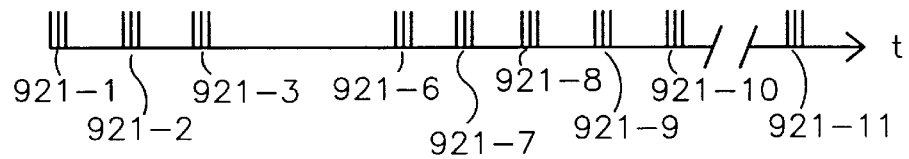
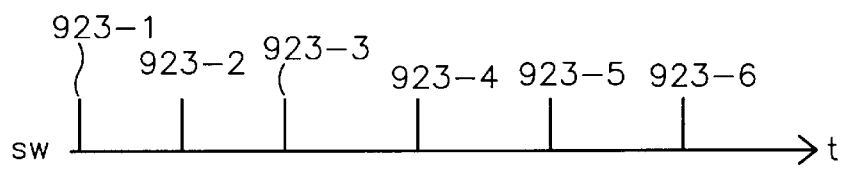
FIG. 10
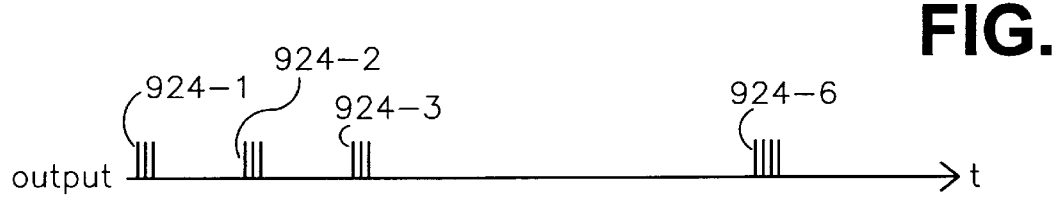

METHOD AND APPARATUS FOR ELECTRICAL STIMULATION OF THE GASTROINTESTINAL TRACT

This application is a division of application Ser. No. 08/990,965, filed Dec. 15, 1997.

FIELD OF THE INVENTION

The invention relates to treatment of gastrointestinal disorders using a method and apparatus for providing electrical stimulation of the gastrointestinal tract.

BACKGROUND OF THE INVENTION

The gastrointestinal tract is responsible for an essential step in the digestive process, the reception of nutrition in the human body. An important element of the digestive process is peristalsis, the coordinated and self-regulated motor activity of the intestinal tract. Peristalsis is accomplished through a coordinated combination of electrical, chemical, neurological and hormonal mediation, as well as possibly other, as yet unknown, mechanisms.

Many diseases and maladies can affect the motor activity of the gastrointestinal tract, causing malfunction of the digestive process. Such diseases include diabetes mellitus, scleroderma, intestinal pseudo-obstruction, ileus, and gastroparesis.

Gastroparesis, for example, is a chronic gastric motility disorder in which there is delayed gastric emptying of solids and/or liquids. Symptoms of gastroparesis may range from early satiety and nausea in mild cases to chronic vomiting, dehydration, and nutritional compromise in severe cases. Diagnosis of gastroparesis is based on demonstration of delayed gastric emptying of a radio-labeled solid meal in the absence of mechanical obstruction. Gastroparesis may occur for a number of reasons. Approximately one third of patients with gastroparesis, however, have no identifiable underlying cause (often called idiopathic gastroparesis). Management of gastroparesis involves four areas: (1) prokinetic drugs, (2) antiemetic drugs, (3) nutritional support, and (4) surgical therapy (in a very small subset of patients.) Gastroparesis is often a chronic, relapsing condition; 80% of patients require maintenance antiemetic and prokinetic therapy and 20% require long-term nutritional supplementation. Other maladies such as tachygastria or bradygastria can also hinder coordinated muscular motor activity of the gastrointestinal tract, possibly resulting in either stasis or nausea or vomiting or a combination thereof.

The undesired effect of these conditions is a reduced ability or complete failure to efficiently propel intestinal contents down the digestive tract. This results in malassimilation of liquid or food by the absorbing mucosa of the intestinal tract. If this condition is not corrected, malnutrition or even starvation may occur. Moreover nausea or vomiting or both may also occur. Whereas some of these disease states can be corrected by medication or by simple surgery, in most cases treatment with drugs is not adequately effective, and surgery often has intolerable physiologic effects on the body.

Presently, however, there is no practically effective device or system to stimulator intelligently alter the muscular contractions of smooth muscle and the gastrointestinal tract in particular. Therefore, there is a need in the art for a system and method to properly stimulate the gastrointestinal tract to thereby treat ineffective or absent electrical muscular activity of the gastrointestinal tract.

An additional problem also faced by any such devices to properly stimulate the gastrointestinal tract involves accurately detecting any gastric arrhythmias. That is, precisely detecting gastric arrhythmias requires first detecting the intrinsic slow wave rate of the gastric tissue. Unless the intrinsic slow wave rates of the gastric tissues are accurately known then there will not be an accurate reference made determining whether there is a bradygastria or tachygastria present.

SUMMARY OF THE INVENTION

It is an object of the invention to provide a method and apparatus for treating patients having dysfunctional gastrointestinal muscle or disorders of smooth muscles elsewhere in the body.

This and other objects are provided by one or more of the embodiments described below. The present invention is a method and apparatus for providing electrical stimulation of the gastrointestinal tract. The apparatus features an implantable pulse generator which may be coupled to the gastric system through one or more medical electrical leads. In the preferred embodiment the leads couple to the circular layer of the stomach. The pulse generator preferably features sensors for sensing gastric electrical activity, and in particular, whether peristaltic contractions as occurring. The present invention particularly solves the problem of accurately detecting gastric arrhythmias by periodically reverting into a sensed intrinsic gastric rhythm mode. In this mode the output of electrical stimulation is adjusted to only occur at an exceedingly slow rate. This slow rate of stimulation thus permits the gastro-intestinal tissues to undergo an intrinsic depolarization so that the underlying intrinsic slow wave rate may be detected.

BRIEF DESCRIPTION OF THE DRAWINGS

The above-described and other aspects of the present invention may be better understood and appreciated with reference to a detailed description of a specific embodiment of the invention, when read in conjunction with the accompanying drawings, wherein:

FIG. 6 depicts the operation of the present invention to detect the underlying gastric rhythm.

FIG. 7 depicts the activity of the device if an intrinsic slow wave is sensed during the sensed intrinsic slow wave mode.

FIG. 8 depicts the activity of the device, after an intrinsic slow wave, to detect whether a tachygastria is present.

FIG. 10 depicts operation of the device in a further mode.

The FIGS. are not necessarily to scale.

DETAILED DESCRIPTION OF THE INVENTION

Figure 1:
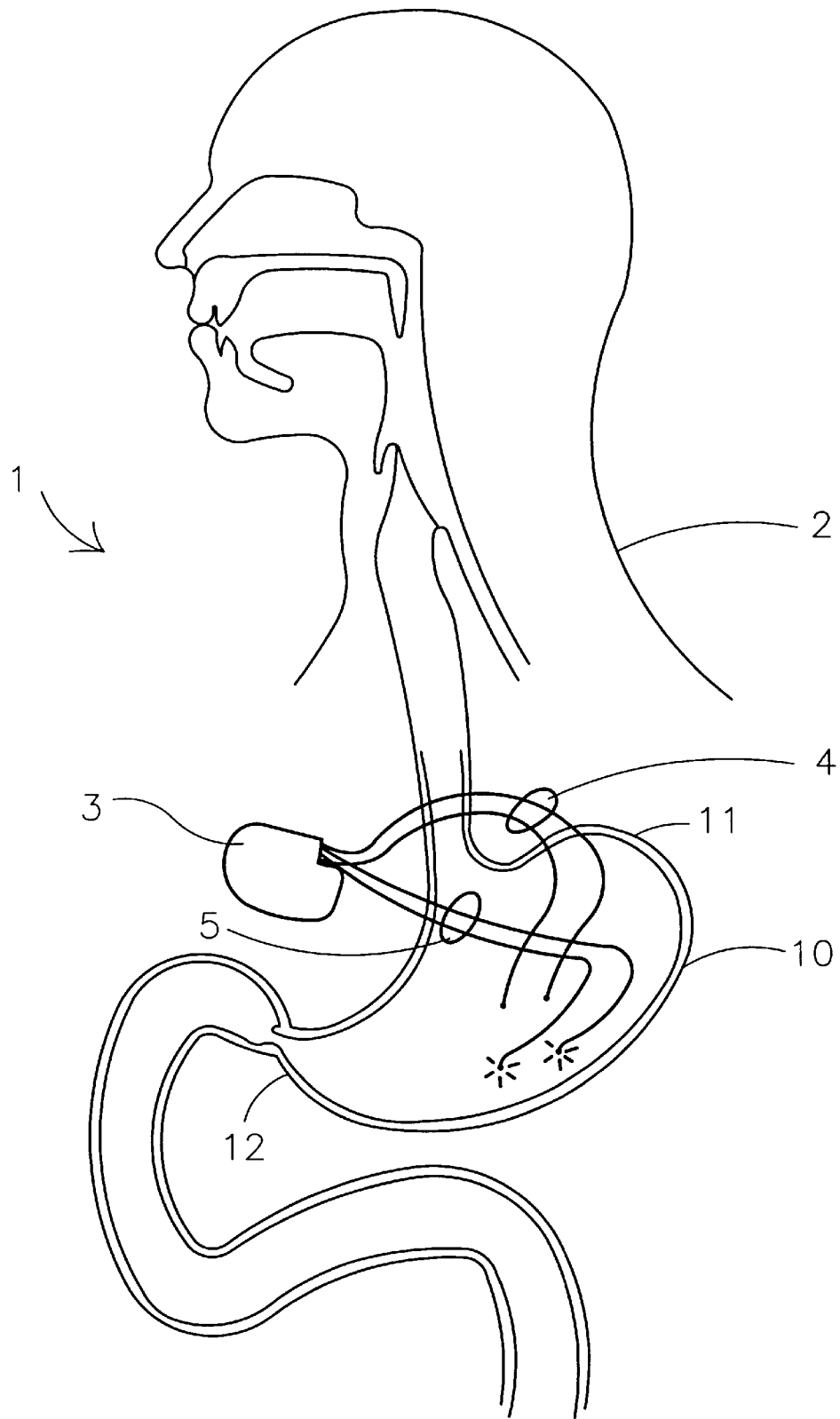
FIG. 1 depicts the apparatus implanted within a patient.

FIG. 1 shows a system 1 implanted in a patient 2. As seen, the system 1 comprises an implantable pulse generator 3 featuring two sets of leads 4, 5 which are coupled to the stomach 10. The first set of leads 4 provide stimulation to the stomach. The second set of leads 5 provide sensing of the gastroelectrical activity of the stomach 10 to the pulse generator 3. In the preferred embodiment, the pulse generator 3 is implanted within the patient 2. As such, the implantable pulse generator 3 features a hermetic enclosure, as is well known in the art. The leads used for both the first set 4 and the second set 5 may be any acceptable lead. In the preferred embodiment, the preferred leads are Medtronic Model No. 4300 intramuscular lead. Of course, other configurations of leads or lead systems may be used, including the use of from only a single lead, a single set of leads (i.e. two), or even the use of three or more sets of leads. Moreover, although shown as being coupled to the stomach it must be understood the present invention may be used along or on any of the other structures and organs along the gastrointestinal tract, including the colon, small intestine, stomach or even the esophagus.

The first set of leads 4 are stimulation leads which conduct stimulation pulses from the pulse generator 3 to the stomach 10. First set of leads 4 are preferably implanted through the serosa at the area within the transition of the corpus and the antrum on the great curvature. Of course, other locations for first set of leads 4 may be used, such as in the fundus, caudud corpus as well as the orad or terminal antrum. The second set of leads 5 are sensing leads which conduct any gastroelectrical activities sensed in the stomach 10 to the pulse generator 3. Preferably the second set of leads 5 are positioned distally in the mid antrum also along the great curvature, although these leads may also be positioned in other locations.

Figure 2:
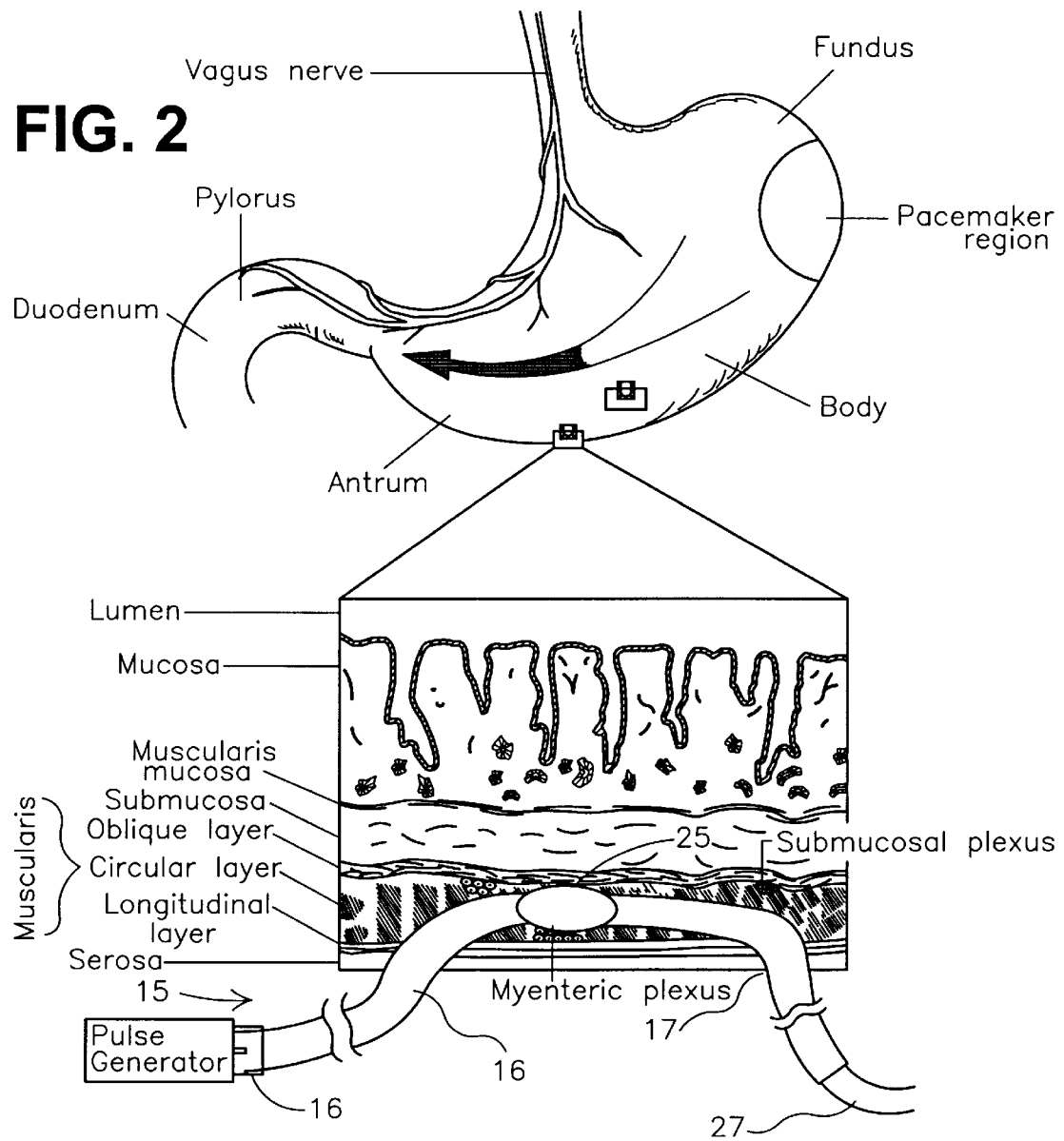
FIG. 2 depicts a detailed view of the stomach muscle showing the electrode of the lead implanted.

FIG. 2 details the preferred positioning of an electrode of a lead within the various layers of the stomach. As seen, the stomach 10 has essentially seven layers of tissue. In the preferred embodiment, the electrode of each lead is positioned into the layers of the stomach muscle as shown. That is, the electrode is positioned such that it intersects both the longitudinal and circular layers. This is believed important by the inventor because in such a manner the electrode is able to also intersect the enteric nervous system of the stomach and be in close contact with the cells of Cajal. This is believed important as research has shown that intramuscular electrodes may effectively stimulate the stomach with less than one one-thousandths of the energy required for serosal electrodes. Of course, other types of electrodes or lead systems may be used, including those which contact only any one of each of the layers of the stomach organ, such as only the mucosa or only the serosa. Moreover, although in the preferred embodiment a pair of unipolar leads are used for stimulation and a second pair of unipolar leads are used for stimulation, other configurations of leads may be used, such as bipolar, tripolar, quadrapolar, as well as any other configuration suitable such as a unipolar lead and can.

Figure 3:
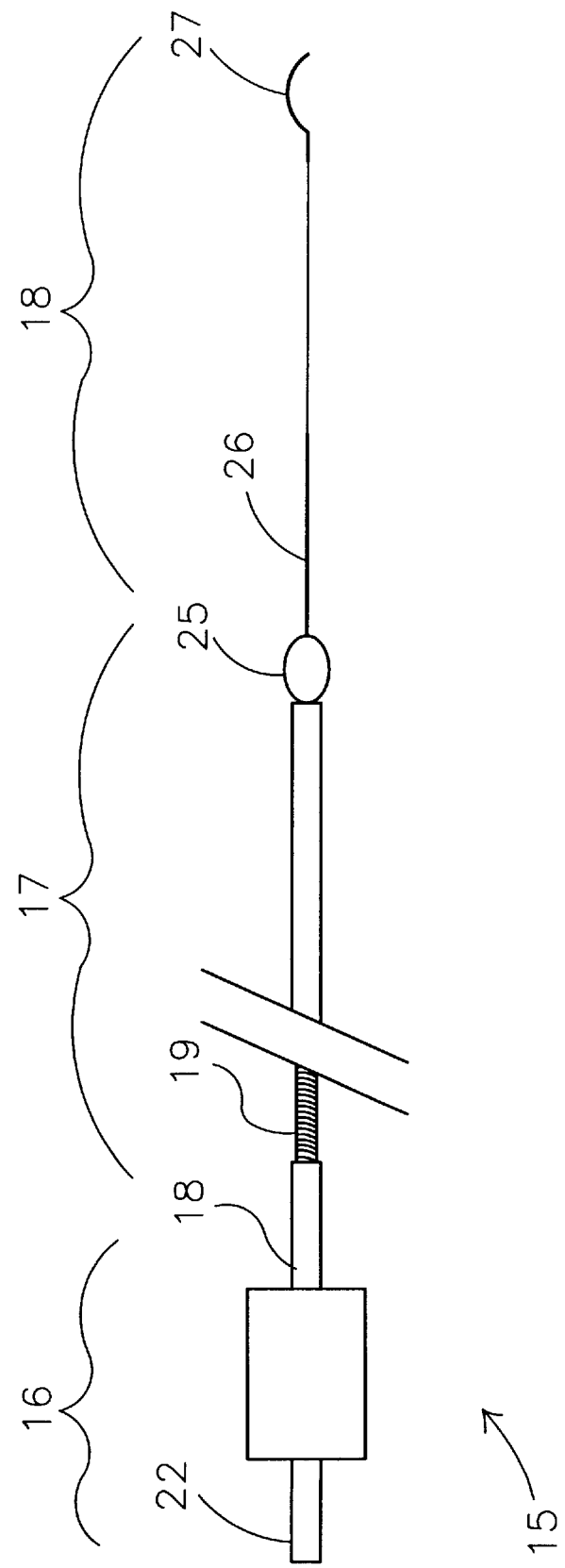
FIG. 3 depicts a plan view of a lead used with the apparatus.

FIG. 3 depicts a plan view of the preferred embodiment lead 15 used in the present invention. As seen, the lead 15 essentially has three sections, connector section 16, body section 17 and fixation section 18. Connector section 16 includes a connector pin 22 to electrically couple the lead 15 into the pulse generator. Any connector pin 22 as well known in the art may be used. Body section 17 includes an electrical conductor 19 surrounded by an electrical insulator 20. In the preferred embodiment electrical conductor 19 is a platinum iridium alloy and electrical insulator 18 is silicone. Of course, other biocompatible materials may also be used. As seen, at the distal end of the body section 17 is an electrode 25. In the preferred embodiment, electrode 25 is a polished platinum iridium alloy. Of course, other materials may likewise be used, such as a porous platinized structure. In addition, the electrode 25 could further feature various pharmaceutical agents, such as dexamethasone sodium phosphate or beclomethasone phosphate in order to minimize the inflammatory response of the tissue to the implanted lead 15. Other agents such as antibiotics may also be used. Located distal to the electrode 25 is the fixation section 18. As seen, fixation section 18 has essentially two piece parts, a suture 26 which is in turn coupled to a needle 27. Needle 27 is preferably curved. In an alternate embodiment suture may feature a fixation coil as is well known in the art to cooperate with the body tissue after implantation to maintain the lead 15 in the position implanted. Of course, other fixation mechanisms may be used, such as fixation discs, as is well known in the art.

Figure 4:
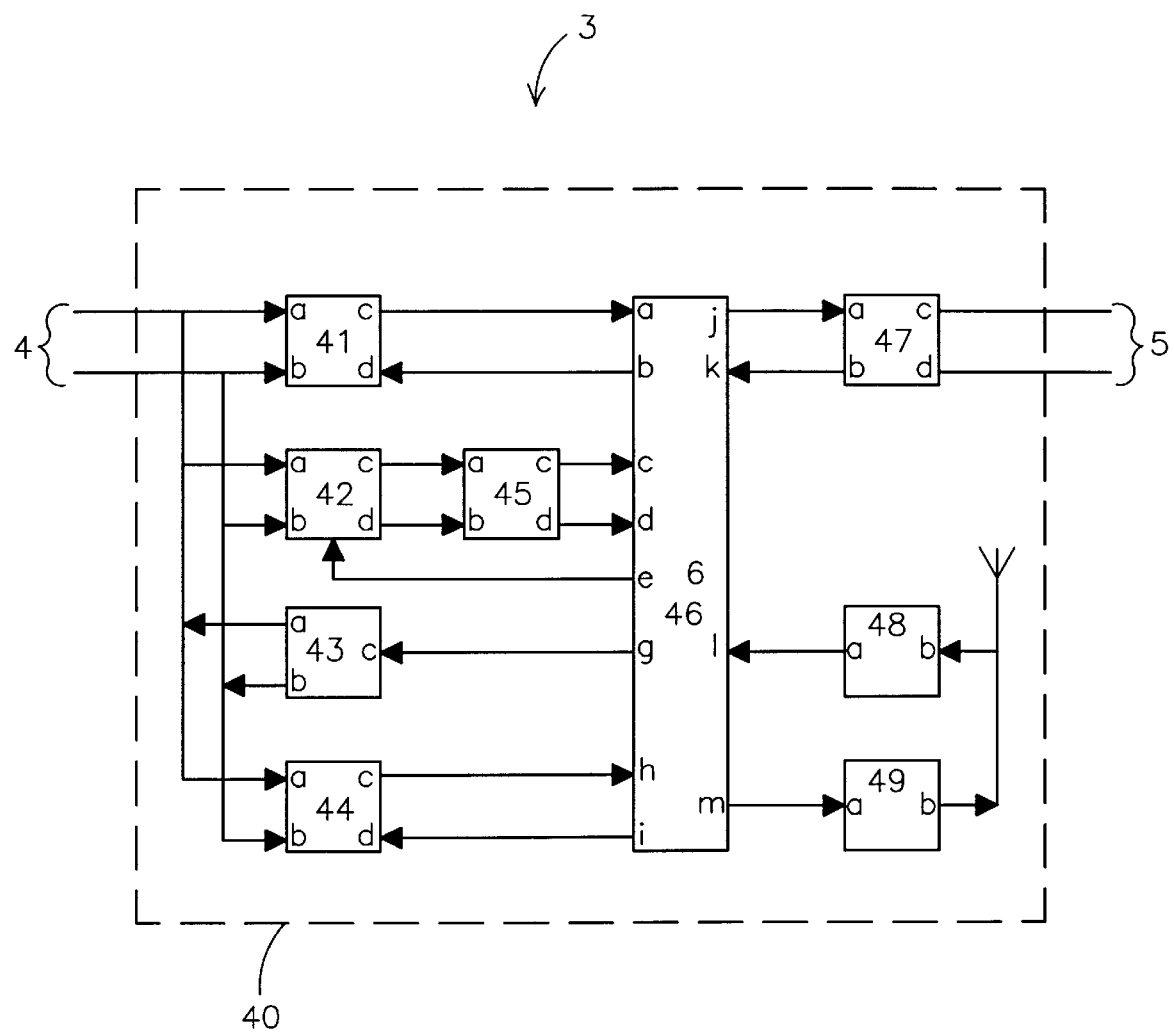
FIG. 4 is a functional block diagram of the pulse generator.

FIG. 4 depicts a functional block diagram of the gastrointestinal pulse generator according to the present invention. As seen, pulse generator 3 is enclosed by hermetic enclosure 40 to the electronics and battery while the device is implanted. Hermetic enclosure may consist of any suitable construction. Pulse generator 3 couples with two sets of leads 4, 5 which are, in turn, coupled to the stomach 10. The first set of leads 4 transmits stimulation pulses from pulse generator 3 to the stomach. The second set of leads 5 provide sensing of the gastroelectrical activity of the stomach 10 to the pulse generator 3. Although in the preferred embodiment the stimulating leads and sensing leads are separate leads, the present invention may also be employed using a combination of lead which both sense and stimulate.

As seen, the sensing leads 4 are coupled into a slow wave detection circuit 41. Slow wave detection circuit 41 includes a band pass amplifier, a slew rate converter and two threshold detectors and is preferably constructed so as to sense the rate of depolarizations in the tissue of the organ between the frequency of approximately 0.017–0.25 Hz. Essentially, such a slow wave detection circuit 41 is similar to those used in a cardiac pacemaker but with several important characteristics. First, the band pass amplifier has a much lower center frequency, preferably on the order of 0.3 HZ when used in the stomach. Of course, the present invention may be used in each of the various organs along the gastrointestinal tract so that the center frequency may be varied accordingly. The slew rate converter operates in a manner well known in the art and generates a signal corresponding to the slew rate of the sensed electrogastrogram. The threshold detectors operates in a manner well known in the art and generate output signals when the sensed input signal is above a threshold level. One threshold detector corresponds to the peak to peak amplitude of the sensed electrogastrogram. The second threshold detector corresponds to the sensed slew rate.

Preferably, the slow wave detection circuit 41 must be able to detect input signals between approximately 30 microvolts and 10 millivolts which have a slew rate between 100 microvolts per/second up to 10 volts per/second with a typical value of 100 millivolts per second. Such a range may be achieved using multiple steps which are controlled by the microprocessor 46 via the input line 46b-41d. To detect the slow wave, both threshold detectors should be coupled using a logical AND configuration. Thus, a signal should then be sent via the output line 41c-46a to the microprocessor 46. The slew rate detector may also include an interference detector specially designed to detect continuous interference, especially at any of the various mains frequencies of power distribution (e.g. 16–400 Hz) so that false sensing is avoided. In an alternative embodiment a second sense amplifier may be provided having a bandpass in the range of expected power field variations in various frequencies of power distribution(e.g. 16–400 Hz). At every cycle the presence of interference is detected. The time interval between two detections is measured and if this time interval corresponds to any of the main frequencies of power distribution which is preprogrammed, then this detection is labeled as interference and the detection on the other amplifier will be simultaneously labeled also as interference detection and not as a valid slow wave.

The band pass amplifier in the detection circuit 41 should be blanked for a period after a sensed event has been received by the microprocessor 46 or just before and during a stimulation pulse is emitted by output stage discussed below. Blanking may be accomplished through either a blanking switch which disconnects the amplifier from the electrodes or through a program performed in the microprocessor. The microprocessor 46 should also ignore sensed output signals during a period after a sensed or paced event. This is similar to a blanking circuit where sensed events during a blanking period do not affect the timing of the pulse generator. In the preferred embodiment, the blanking period for slow wave detection is on the order of between 0.5 to 4.0 seconds.

Generally speaking, the blanking period decreases with increasing slow wave frequency. The blanking period algorithm is controlled by the microprocessor. The blanking period algorithm operates such that when the slow wave interval is shortened the blanking period is also shortened. This shortening may be performed in any manner, for example, in a linear fashion or in some other more complex monotonous fashion. After the blanking period, during a certain timing window, the microprocessor 46 is able to receive slow wave detection signals, which will not restart the pulse generator timing circuit, but will instead be interpreted as interference by the microprocessor 46. This timing window, interference detection timing window, may be up to seven seconds in duration after the sensed or paced event, preferably it is 100 milliseconds. To be precise, the combined blanking period and interference detection windows are shortened. Shortening may occur in any manner desired, i.e. in a linear fashion between a preset high or a preset low value or along a non-linear manner. The shortening of the combined blanking and interference detection interval will not occur once the combined blanking and interference detection window reaches a programmed value, such as 2.5 s. This combined blanking window may also be programmed to be turned off such that it does not change in response to sensed physiologic signals. In all circumstances, however, the interference detection window remains equal to at least 100 ms. For example, the rationale is that the typical main frequencies of power distribution are 50 Hz, 60 Hz, 400 Hz and 16.33 Hz. The lower harmonic for 1633 Hz is 8 Hz which corresponds to an interval of 125 ms. Of course the exact length of time for each period may be programmed by the physician. Moreover, each of the periods may be further made to be automatically adjusted based on the sensed electrical activity.

As seen in FIG. 4, blanking switch 42 couples sensing electrodes 4 to amplifier 45 to detect high frequency spike activity. The operation of blanking switch 42 causes the amplifier 45 to be connected to the sensing electrodes 4 once an intrinsic deflection or slow wave has been detected by slow wave detection circuit 41 or a stimulus has been emitted by output stage 47. Preferably, this occurs after a short delay. Blanking switch 42 is closed between 0.5 to 2 seconds after these events and opens roughly 5 to 7 seconds later or at approximately 30% of the intrinsic event interval. As seen, the switch is controlled via the line 46e-42e.

The detection circuit for the high frequency spike activity detector consists of a bandpass amplifier having the center frequency at approximately 300 Hz. As discussed above, however, the center frequency will vary for different organs. The amplifier is followed by two threshold detectors, the first detector detects peak to peak amplitude while the second detector detects slew rate. Both detectors are coupled using a logical AND configuration. The detector pulses are counted, and the interval between pulses is measured. If the interval corresponds to the intervals of the mains frequencies of power distribution or any of their harmonies, i.e. 20 ms or 10 ms, they are rejected. If the number of pulses exceeds a pre-programmed value, then a contraction is indicated. The counter is provided to store in the memory the time of occurrence of the contraction. The number of pulses corresponding to each contraction may be counted and tallied to determine the strength of the contractions. In the present embodiment 3–5 pulses correspond to a weak contraction; 6–8 pulses correspond to a moderate contraction; 9 or more pulses correspond to a strong contraction. Each of these values, of course, may be programmed and the exact number of pulses will vary due to the implementation.

Also coupled to the sensing electrodes 4 is an AC current generator 43. This AC current generator 43 is part of a plethysmorgraphy circuit. Overall, the plethysmography circuit is present to provide a means for sensing mechanical activity of the underlying tissue. That is, whereas the spike activity in the electrogastrogram may be used to sense contraction, the contraction may also be sensed using the plethysmography circuit. Plethsmography circuit is comprised from AC current generator 43, amplifier, modulator and ADC converter 44 as well as a portion of the microprocessor 46. The AC current generator 43 is switched on via signal from microprocessor 46 once a slow wave is detected or a pacing stimulus is emitted. It is switched off roughly 10 seconds after being switched on also from the same line or signal from the microprocessor 46. The AC current generator 43 amplitude and frequency are programmable via microprocessor 46. The frequency should be such it is not detected by amplifiers 41, 45, e.g. 1 kHz. If synchronous detection by amplifier 41 occurs at the end of the blanking period, then the amplitude and/or the frequency of the AC current generator 43 is adjusted by the microprocessor 46 to avoid subsequent detection of the generated AC current.

Turning now to the amplifier, the modulator and ADC converter 44, the AC voltage caused by the injection of AC current generator 43 is amplified and demodulated and converted in order to detect impedance changes caused by contractions of the underlying tissue. The ADC converter digitizes the amplitude of the demodulated signal. The digitized signal is transmitted via line 44c-46h to the microprocessor 46. The microprocessor 46 analyzes the signal pattern by comparing it with one or more templates to identify it as a contraction as well as to reject interference or signals generated by postural changes or vomiting. This template comparison is done synchronously to the detection of the slow wave. Line 46i-44d is used to control the amplifier and ADC from the microprocessor 46.

The microprocessor 46 handles all timings and data storage of the pulse generator and may be of any suitable design. In the preferred embodiment, a microprocessor 46 such as that used in the Thera I series of Medtronic pacemakers is used. The description of the microprocessor 46 function is described in the section below which details the operation of the algorithm used in the present invention.

Stimulation pulses are generated by the output stage 47. In the preferred embodiment, the output stage 47 generates pulse trains. It should be understood many types of pulse trains or stimulation pulses may be used including constant current or constant voltage outputs, or a mixture of both. The output pulses are transported to the gastrointestinal tissue via medical electrical leads 5 and thus to the stomach.

Turning again to the output stage 47, when an output pulse is to be delivered, its amplitude, pulse width and duration and frequencies are controlled via lines 46$j$-47$a$. If it is a burst of stimuli, the frequency and duration are controlled through the same line while a burst finished signal is sent to the microprocessor 46 via output line 47$b$-46$k$.

Programmability to the pulse generator 3 is achieved through receiver-demodulator 48 and transmitter 49. As seen, each of these devices is coupled to the microprocessor 46. The receiver-demodulator 48 and transmitter 49 are similar to those used in cardiac pacemakers.

The basic parameter settings such as sensitivity (peak voltage or slew rate), refractory, blanking, output pulse amplitude, pulse width, escape interval and ratio, escape interval to a stimulation interval, are stored in the memory of the microprocessor 46. Default values are also stored. These values can be read from memory and sent to a receiver via the transmitter.

Figure 5:
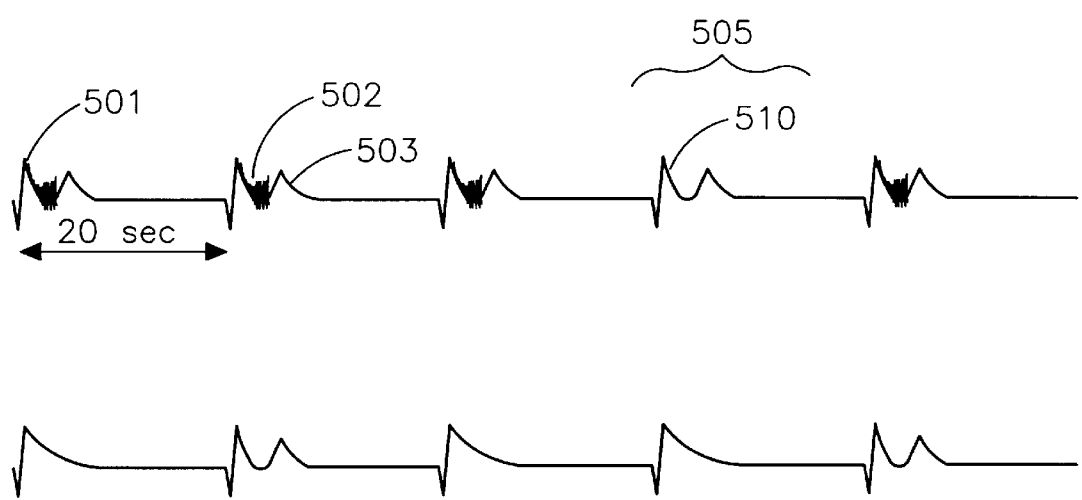
FIG. 5 is an electrogastrogram of the gastrointestinal system.

FIG. 5 shows an electrogastrogram of the stomach in a human. As seen, this intrinsic gastroelectric activity has two distinct components. The first component 501 is a low-frequency, rhythmic depolarization termed slow waves. Superimposed on the slow wave is a high frequency spike activity 502 which corresponds to mechanical contractions of the organ. In the human stomach slow waves are regular, omnipresent depolarizations at 3 cycles/min. (0.05 Hz) that commence high on the greater curvature of the stomach, in the region referred to as the pacemaker region, and propagate aborally, as depicted in FIG. 2.

The normal frequency range for the slow wave in the stomach is between 2.7–3.4 bpm. In clinical situations this value may vary anywhere between 1–15 bpm. High frequency slow wave activity (called tachygastria) does not permit contraction of the stomach readily and may even results in a gastroparesis. In the presence of excessively slow or even absent slow waves (called bradygastria) motility is reduced.

Slow waves and the corresponding spike activity may become irregular or uncoupled or both, thereby preventing the appearance or organization of regular, normally propagated contractions that constitute normal motility. Contractions cannot occur without gastric electrical response activity which is in turn regulated by the electrical control activity. Any disruption in this delicate sequential order may lead to delayed gastric emptying. An example of such an occurrence is shown in complex 505.

The spike activity occurs incidentally for a few of the slow waves while the patient is in a fasting or non-eating condition. This is termed Migratory Motor Complex ("MMC") phase I. Immediately prior to a meal, typically 30 mins, MMC I changes into MMC phase II. During this phase the number of slow waves having spike activity increases. Once the meal or eating has begun and up to 120 mins after the meal each further slow wave also has a spike activity component. This condition is called MMC phase III.

As seen in this complex a slow wave 510 occurs which is not followed by any high frequency spike activity. The absence of such activity indicates there is no longer any peristaltic contraction which will occurs, i.e. gastric emptying is delayed.

An example of the operation of the present invention to detect the underlying gastric rhythm is depicted in FIG. 6. As seen, slow waves 920-1, 920-2 and 920-3 occur in response to the delivery of electrical pulse trains 921-1, 921-2 and 921-3. Following the pulse train 920-3 the device enters into the sensed intrinsic gastric depolarization mode. While in this mode the rate of pulse trains delivered is decreased. As seen, the pulse trains had previously been delivered at a rate corresponding to 3 per minute, once every 20 seconds. But while in this mode the delivery is decreased to once per minute. As seen, because no further slow waves occur following the delivery of pulse train 920-3 until the expiration of the 60 seconds time period, an additional pulse train is delivered 921-4 causing a corresponding evoked slow wave to occur 920-4. In the preferred embodiment the device continues to remain in the sensed intrinsic slow wave mode for one additional cycle and again a pulse train is not scheduled for delivery until 60 seconds expires. In the present example the intrinsic slow wave is not sensed during this cycle and a pulse train is again delivered upon its expiration 921-5 thereby causing a corresponding slow wave 920-5. At this time the mode is disconnected and the device returns to the rate of previous stimulation and delivers stimulating pulse trains 921-6 and 921-7.

FIG. 7 depicts the activity of the device if an intrinsic slow wave is sensed during the sensed intrinsic slow wave mode ("SISW"). Similar to that discussed above slow wave 920-1, 920-2 and 920-3 are evoked by the delivery of pulse trains 921-1, 921-2 and 921-3 respectively. Upon entering the sensed SISW mode the device lengthens the escape interval to 60 seconds as depicted at 922 and 923. During this 60 seconds period intrinsic slow waves are sensed. This information is used to adjust, thereafter, the rate of stimulation. In the preferred embodiment the device now begins stimulating again at a rate slower than that used previously. This is depicted with pulse trains 921-5, 921-6 and 921-7 and the corresponding evoked slow waves 920-5, 920-6 and 920-7.

FIG. 8 depicts the activity of the device, after an intrinsic slow wave, to detect whether a tachygastria is present. Tachygastria refers generally to any unusual fast intrinsic slow waves. From the patient's perspective tachygastria often coincides with nausea or vomiting or both. Such condition may occur intermittently and thus such device which continuously stimulates the stomach as if it were in tachygastria would be both inefficient, from an energy standpoint, as well as non-physiologic, delivering a therapy which did not correspond to the actual patient condition. In response to this difficulty, the present invention further features the ability to periodically detect whether a tachygastria is occurring and thereafter adjust or deliver the appropriate electrical stimulation. As seen in FIG. 8, slow waves 920-1, 920-2 and 920-3 are evoked slow waves which occur in response to the delivery of electrical pulse trains 921-1, 921-2 and 921-3. Following the pulse train 921-3 the device enters into the sensed detect tachygastria mode. While in this mode the pulse trains are not delivered such that an accurate sensing of the intrinsic slow wave rate may be performed. As seen, these intrinsic slow wave rates are shown as 920-4 and 920-5. As seen, these would indicate tachygastria is present as they are occurring at a naturally fast rate. Once such tachygastria is detected, the device then turns and proceeds into the tachygastria mode in which it delivers stimulation at an increased rate, i.e. a rate often faster than the detected tachygastria. In the preferred embodiment this rate is set at 10% greater than the detected tachygastria rate, although other rates of stimulation between 1%–100% greater than the detected tachygastria rate may be chosen. Such tachygastric stimulation occurs for a preset period of time at the expiration of which the device then returns to the normal mode of stimulation, shown here as pulse trains 921-11. This preset period of time is typically set for between 1–5 minutes, although other time periods may also be chosen. In addition, the entire length of treatment may be controlled by other sensed parameters of the patient. Once tachygastria is detected and the preset time of stimulation is delivered, the device again reverts to a detected tachygastria mode, and again inhibits delivery of electrical stimulation so as to be able to accurately detect intrinsic slow wave depolarization.

Figure 9:
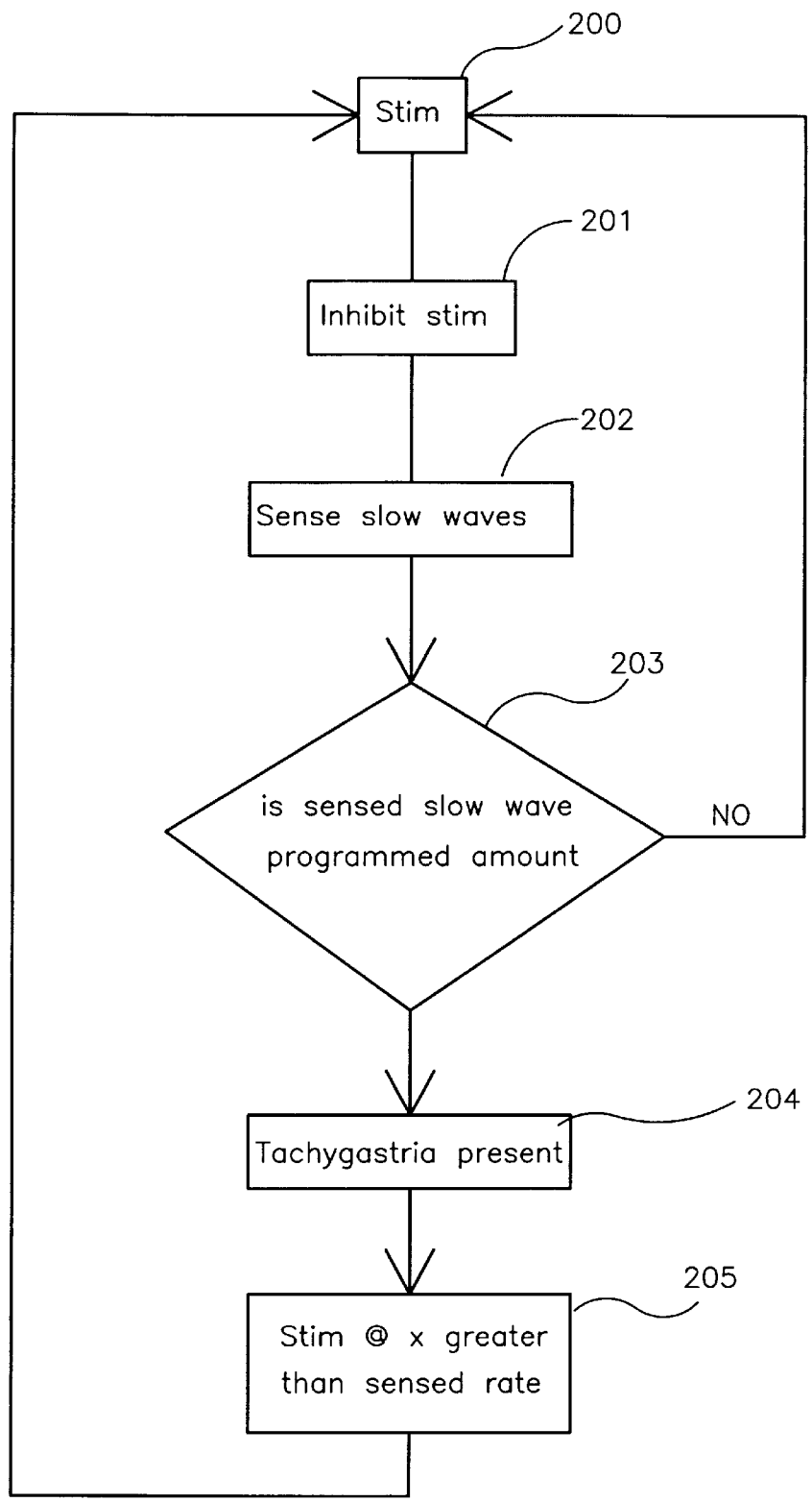
FIG. 9 depicts a flow chart of the method of detecting tachygastria as illustrated in FIG. 8.

FIG. 9 depicts a flow chart of the method of detecting tachygastria as illustrated in FIG. 8. At step 200 the device is in normal stimulating mode and delivers electrical pulse train stimulation as indicated by the patient's condition and is programmable by the physician. Thus in this step stimulation may be continuous or on demand or in any other mode as desired. As discussed above, such stimulation may be in any form as desired, but preferably consists of a pulse train delivered at a rate of between 7–27 bpm with 12 bpm preferred. The pulse train preferred consists of two pulses, each the pulse having an amplitude, a pulsewidth and an interpulse interval. The interpulse interval may be anywhere between 6–600 ms in length with 60 ms preferred, the amplitude may be between 1–50 milliamps with 5 milliamps preferred and pulsewidth may be between 3–1000 microseconds with 330 microseconds preferred. Moreover, although the pulse train consisting of two pulses is preferred, any number of pulses between 1–100 may be used. As discussed above, the exact parameters selected depend not only on the organ to be stimulated but also upon the patient's physiology as well as on the preference of the physician attending.

When the device proceeds to step 201 it enters a detected tachygastria mode and thus inhibits stimulation. Next, the device at step 202 senses the intrinsic slow waves which would occur in the absence of stimulation. This sensing may occur for any desired period of time and preferably would occur for a period of 3 slow waves or 60 seconds whichever occurs first. Once a desired sampling of intrinsic slow wave has been sensed the device determines at step 203 whether the sensed intrinsic slow wave rate is greater than the programmed rate. This programmed rate is set as the rate at which tachygastria is defined as present, and preferably is set at greater than 4 bpm and most preferably greater than 6 (or conversely at an interval of less than 15 seconds or more preferably less than 10 seconds). If the slow wave rate is greater than the programmed amount, the device at step 204 deems a tachygastria is present, otherwise the device recycles itself back to step 200. If, however, at step 204 tachygastria is deemed present, then the device proceeds to step 205 and delivers stimulation at a rate greater than the sensed intrinsic rate. As discussed above, this rate preferably is 10% greater than the sensed intrinsic rate, although the particular rate may be anywhere between 1–100% greater. Moreover, besides the pulse train rate which can be adjusted, the particular pulse train characteristic set to treat tachygastria may further be adjusted, and such tachygastria stimulation may entail higher energy of the individual pulses, increased number of pulses per pulse train, mono-, bi-, or tri-phasic pulses in the pulse train, etc. as desired by the clinician. Such tachygastria treatment is delivered for a preprogrammed period of time, as discussed above. Once such time has elapsed the device recycles back to step 200.

FIG. 10 depicts operation of the device in a further mode. In particular, as shown in FIG. 10, the device must periodically measure the intrinsic slow wave interval. Thus may only be achieved by periodically causing the electrical stimulation to not be delivered so that the intrinsic slow wave may be sensed. Of course, the device must also provide the ability to eventually deliver electrical stimulation should no intrinsic slow wave occur once the scheduled delivery of stimulation is ceased. Thus, as shown in this FIG., the device further features an escape interval and an ultimate escape interval. The escape interval is the greatest possible interval of time during which, for normal operation, the device will wait to sense the intrinsic slow wave before delivering electrical stimulation. The ultimate escape interval is an escape interval which is only operable during the time in which the device seeks the intrinsic slow wave so as to adjust the escape interval and essentially ensures that if no intrinsic slow wave is ever sensed while the device seeks intrinsic slow wave, electrical stimulation will be delivered. This may be seen to occur in FIG. 10. Slow waves 923-1, 923-2 and 923-3 occur in response to the delivery of electrical pulse trains 924-1, 924-2 and 924-3. After 924-3 the device enters into a sense intrinsic slow wave interval mode. During this time electrical stimulation is no longer delivered. As seen, during this period intrinsic slow waves 923-4 and 923-5 are detected. Once these have been detected, the device uses this information to reset the escape interval such that electrical stimulation will occur in a fashion more corresponding to the underlying physiology. Thus pulse trains 924-6 are delivered at a new period of time after sensed slow wave 923-5, thereby evoking slow wave 923-6.

Figure 11:
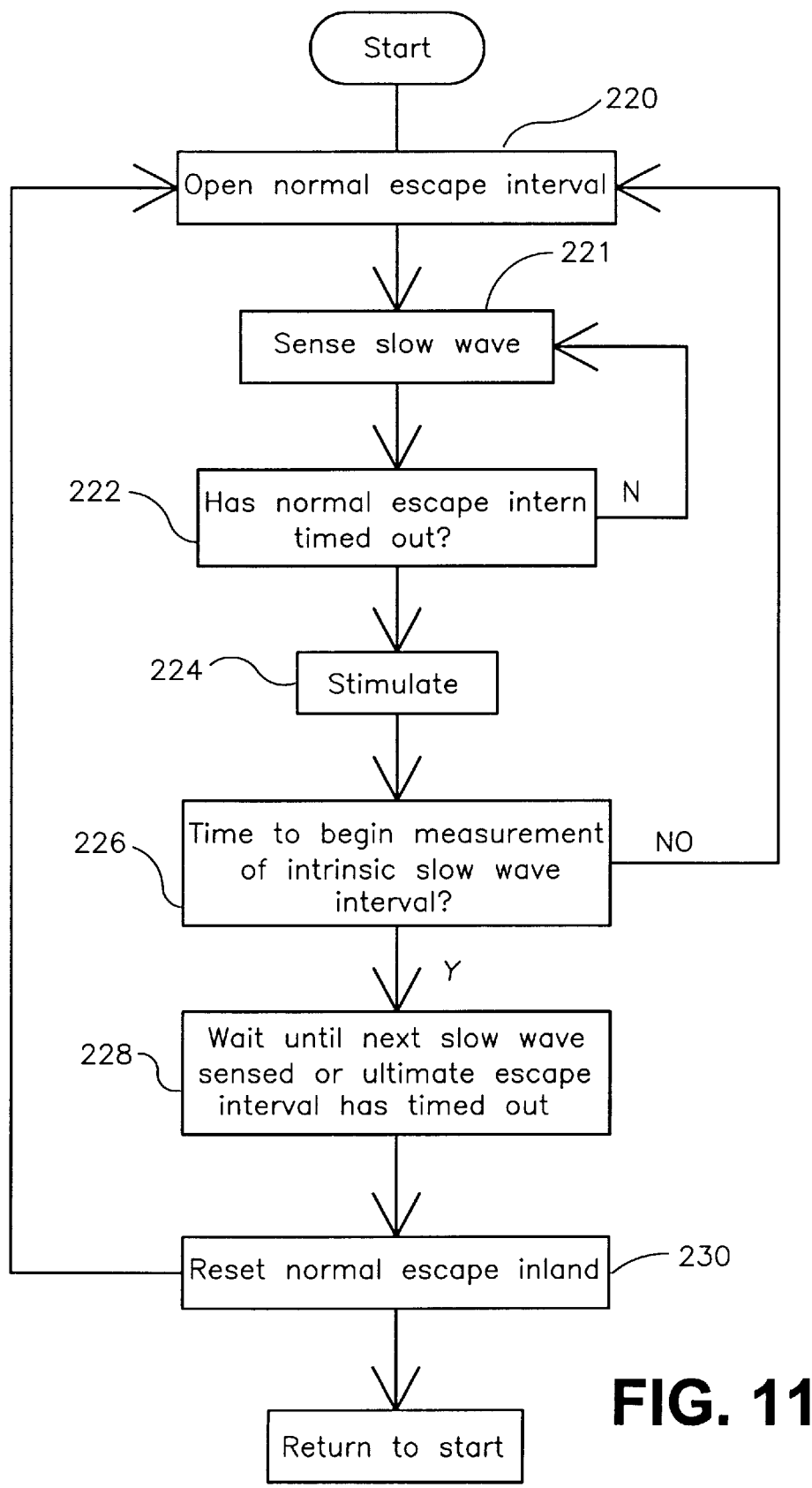
FIG. 11 depicts a flow chart illustrating a portion of the device which is also depicted in FIG. 10.

FIG. 11 depicts a flow chart illustrating a portion of the device which is also depicted in FIG. 10. As seen, during normal operation at step 220 the device opens the normal escape interval. As discussed above, at the end of such an interval the device would deliver electrical stimulation. Next, at step 221 the device senses for intrinsic slow waves. At step 222 the device determines whether the normal escape interval is timed out, if it is not, the device recycles again to step 221. If the normal escape interval is timed out, then the device proceeds to step 224 and delivers the scheduled electrical stimulation. Next, the device proceeds to block 226 and determines whether it is time to begin measurement of the intrinsic slow wave interval. If it is not, the device then recycles back to step 220, but if it is time the device proceeds to step 228. At step 228 the device opens the ultimate escape interval and senses whether the intrinsic slow wave occurs. The ultimate escape interval is either reset upon detection of a sensed slow wave, or is halted after the programmed period of time or number of sensed intrinsic slow waves has been achieved. If, however, no such intrinsic slow waves have been sensed during the ultimate escape interval, then the device would deliver electrical stimulation at the end of such an interval. As seen, if no sensed slow intrinsic slow waves occur, then the device exits this mode and again reverts back to the normal mode of operation beginning at step 220. Otherwise the device moves down to step 230 and uses the information about the intrinsic slow wave to reset the normal escape interval. Once updated, the device then reverts back to the normal mode of operation in step 220.

While the present invention has been described in detail with particular reference to a preferred embodiment, it will be understood variations and modifications can be effected within the scope of the following claims. Such modifications may include substituting elements or components which perform substantially the same function in substantially the same way to achieve substantially the same result for those described herein.

What is claimed is:

1. An apparatus for providing electrical stimulation to the gastrointestinal tract comprising:

means for electrically coupling to the gastrointestinal tract;

a pulse generator coupled to the means for electrically coupling to the gastrointestinal tract, the pulse generator emitting stimulation pulse trains at a first rate;

means for periodically inhibiting the emission of stimulation pulse trains at the first rate and emitting stimulation pulse trains at a second rate, the second rate slower than the first rate; and means for sensing slow wave gastrointestinal electrical activity, the slow wave sensor coupled to the means for electrically coupling to the gastrointestinal tract, the slow wave sensor emitting a slow wave gastrointestinal electrical activity signal upon the sensing of slow wave gastrointestinal electrical activity within a preset frequency range.

2. The apparatus of claim 1 further comprising means responsive to the sensing means for adjusting the first rate.

3. The apparatus of claim 1 wherein the means for sensing slow wave gastrointestinal electrical activity further comprise means for sensing tachygastric activity, the means for sensing tachygastric activity emitting a tachygastric activity signal upon the sensing of intrinsic tachygastric activity.

4. The apparatus of claim 3 wherein the pulse generator further comprises tachygastric stimulation means for emitting tachygastric stimulation in response to the emission of the tachygastric activity signal.

5. The apparatus of claim 4 wherein the tachygastric stimulation means emits tachygastric stimulation at a rate greater than a rate of the tachygastria activity signal.

6. The apparatus of claim 1 wherein the pulse trains emitted at the first rate comprises a pulse train, the pulse train having an amplitude, a pulsewidth and an inter pulse interval.

7. The apparatus of claim 6 wherein the interpulse interval is between approximately 6–600 ms in length.

8. The apparatus of claim 7 wherein the interpulse interval is approximately 60 ms.

9. The apparatus of claim 6 wherein the amplitude is between approximately 1–50 milliamps.

10. The apparatus of claim 9 wherein the amplitude is approximately 5 milliamps.

11. The apparatus of claim 6 wherein the pulsewidth is between approximately 3–1000 microseconds.

12. The apparatus of claim 11 wherein the pulsewidth is approximately 330 microseconds.

13. The apparatus of claim 6 wherein the pulse train having between approximately 1–100 pulses.

14. An apparatus for providing electrical stimulation to the gastrointestinal tract comprising:

means for electrically coupling to the gastrointestinal tract;

a tachygastric sensor for sensing intrinsic tachygastric activity, the tachygastric sensor coupled to the means for electrically coupling to the gastrointestinal tract, the tachygastric sensor generating a tachygastric activity signal for transmission through the electrical coupling means upon the sensing of intrinsic tachygastric activity;

a non-tachygastric sensor for sensing intrinsic non-tachygastric activity, the non-tachygastric sensor coupled to the means for electrically coupling to the gastrointestinal tract, the non-tachygastric sensor generating a non-tachygastric activity signal for transmission through the electrical coupling means upon the sensing of intrinsic non-tachygastric activity;

a pulse generator coupled to the means for electrically coupling to the gastrointestinal tract, the pulse generator, in response to receiving the tachygastric activity signal through the electrical coupling means, emitting tachygastric stimulation pulse trains, the pulse generator, in response to receiving the non-tachygastric activity signal through the electrical coupling means, inhibiting the emission of tachygastric stimulation pulse trains.

* * * * *